United States Patent
Sointula et al.

(10) Patent No.: US 10,935,537 B2
(45) Date of Patent: Mar. 2, 2021

(54) SOIL MOISTURE AND ELECTRICAL CONDUCTIVITY PROBE

(71) Applicants: Erkka Sointula, Salo (FI); Peter Ellegaard, San Diego, CA (US)

(72) Inventors: Erkka Sointula, Salo (FI); Peter Ellegaard, San Diego, CA (US)

(73) Assignee: AQUASPY, INC., San Diego, CA (US)

( * ) Notice: Subject to any disclaimer, the term of this patent is extended or adjusted under 35 U.S.C. 154(b) by 298 days.

(21) Appl. No.: 14/952,091

(22) Filed: Nov. 25, 2015

(65) Prior Publication Data

US 2019/0257809 A1    Aug. 22, 2019

(51) Int. Cl.
    *G01N 33/24*        (2006.01)
    *G01N 27/22*        (2006.01)
    *G01N 33/00*        (2006.01)

(52) U.S. Cl.
    CPC .......... *G01N 33/24* (2013.01); *G01N 27/223* (2013.01); *G01N 33/0098* (2013.01)

(58) Field of Classification Search
    CPC ............. G01N 33/24; G01N 2033/245; G01N 33/246; G01N 27/223
    See application file for complete search history.

(56) References Cited

U.S. PATENT DOCUMENTS

| | | | | |
|---|---|---|---|---|
| 5,353,008 A * | 10/1994 | Eikenberry | .......... | A42B 3/0453 2/422 |
| 6,756,793 B2 * | 6/2004 | Hirono | ............... | G01R 27/2605 324/690 |
| 10,060,873 B2 * | 8/2018 | Buss | .................... | G01N 27/223 |
| 2010/0301877 A1 * | 12/2010 | Paterson | ............. | G01N 33/246 324/664 |
| 2014/0249520 A1 * | 9/2014 | Ghaffari | ............. | A61N 1/36135 606/34 |
| 2015/0096368 A1 * | 4/2015 | O'Brien | .................... | E02D 1/00 73/32 A |
| 2016/0025678 A1 * | 1/2016 | Kurup | .................... | G01N 27/48 205/794 |
| 2016/0295819 A1 * | 10/2016 | Porter | .................... | A01G 25/16 |
| 2017/0030852 A1 * | 2/2017 | Portmann | ............. | G01R 27/26 |

* cited by examiner

*Primary Examiner* — Herbert K Roberts
*Assistant Examiner* — John M Royston
(74) *Attorney, Agent, or Firm* — Steins & Associates, P.C.

(57) ABSTRACT

A Soil Moisture and Electrical Conductivity Probe. The soil moisture probe employs brass ring pairs, wherein each pair incorporates dual feedpoints. There is a single main control circuit for operating the plurality of sensor ring pairs in a multiplexed approach. In order to allow for multiplexed operation, each sensor ring pair includes a signal tuning assembly. The signal tuning assembly includes apparatus for attenuating the signal noise at each sensor ring pair, as well as apparatus for matching the ring-pair to ring-pair lead impedence. The temperature of each ring pair is individually detected to improve the accuracy of all of the sensor ring pairs. This temperature sensing is accomplished by multiplexing a single reference voltage with all of the sensor rings, and by implementing a thermistor at each sensor ring pair.

17 Claims, 7 Drawing Sheets

SOIL MOISTURE AND ELECTRICAL CONDUCTIVITY PROBE

This application is filed within one year of, and claims priority to Provisional Application Ser. No. 62/084,491, filed Nov. 25, 2014.

BACKGROUND OF THE INVENTION

1. Field of the Invention

This invention relates generally to agricultural monitoring apparatus and, more specifically, to a Soil Moisture and Electrical Conductivity Probe.

2. Description of Related Art

As global population continues to grow, the need for an analytical, scientific approach to crop growth has become of increasing importance. While many environmental conditions are variable, and are only controllable in the context of choice of locale for a particular planting, some can be controlled.

One environmental condition affecting crop growth and yield that has long been sought to be "controlled" is that of irrigation. All farmers know that a key to a good crop is to irrigate enough to promote good growth, but not so much as to overwater the plants or to dilute fertilizers and/or soil nutrients.

For the small "family" farm, optimizing irrigation, while inexact, is achievable through persistence and long-term direct experience. This situation does not typically apply to the large "corporate" farm, however. The corporate farm is much larger than the traditional family farm, and consists of enormous planted areas that can only be planted, tended and harvested by mechanized means.

The irrigation of these corporate fields is handled by automated systems that dispense water (at times mixed with fertilizer and other compounds) over the planted areas, usually by extremely long irrigation arms pivoting around the field. These irrigation arms now have the ability to regulate the amount of water dispensed in a very controlled fashion along the length of the arm, as well as for particular arc sectors as the arm pivots around the field.

The key to the efficient operation of these sophisticated irrigation arms is the ability to detect and report the actual moisture levels in the soil being irrigated. This data can then be fed to the irrigation system for the purpose of responsively adjusting the amount of irrigation water dispensed over a particular portion of the planted field. Soil moisture sensors have continued to evolve for just this purpose. FIG. 1 depicts a conventional version of just such a device.

FIG. 1 is a cutaway side view of a conventional soil moisture probe 10[1]. The probe 10 is usually an elongate, cylindrical device that is buried beneath the soil 8 at strategic locations around the monitored area of a field. A control conduit 20 (generally a multi-filament cable having a waterproof cover) interconnects the probe 10 and a central control unit (not shown). The control unit directs the operation of the network of probes 10, records their soil moisture data (and usually other parameters), and transmits the data wirelessly to the group operation the probes 10.

[1] As used throughout this disclosure, element numbers enclosed in square brackets [ ] indicates that the referenced element is not shown in the instant drawing figure, but rather is displayed elsewhere in another drawing figure.

The probe 10 has a cylindrical housing 12, typically made from a section of PVC pipe (or other suitable material). The typical housing 12 has a wall thickness of approximately 2.4 mm, to insure sufficient structural integrity to protect the internal electronics against crushing or other intrusion from its environment. The ends of the housing 12 are capped and sealed.

A sensor assembly 14 is housed within the sealed housing 12, and in electrical communication with the wiring in the control conduit 20. The interstitial chamber 18 (i.e. the void between the sensor assembly 14 and the interior walls of the housing 12) is typically left empty (or filled with a suitable gaseous material), so that the operation of the sensor assembly 14 is not obstructed, and further so that the probe 10 can be disassembled, such as for maintenance or repair.

The sensor assembly 14 consists of a non-metallic base frame 16 extending over substantially the entire length of the interior of the housing 12. Along the length of the base frame 16 are positioned a series of sensor subassemblies 22A. Each sensor subassembly 22A has a sensor ring pair 24 and a measurement circuit 26. The sensor ring pairs 24 are generally made from segments of brass arranged so that a each ring (which is half of a sensor ring pair 24) has the opposite polarization of its partner ring. This creates an EMF field (actually doughnut-shaped) around that ring pair 24 that can be measured to determine the electrical conductivity of the soil 8 through which each EMF field passes. The conductivity of the soil 8 surrounding each ring 24 is proportional to the amount of moisture that is in the soil 8 surrounding the ring pair 24.

The sensor subassemblies 22A are in regular, known, spaced relation along the base frame 16. By burying the probe 10 aligned vertically at a known depth, it is possible, then, to measure the conductivity of the soil 8 at selected depths (e.g. D1, D2, D3, etc.) in close proximity to the probe 10.

A problem with the conventional sensor approach is that each sensor ring pair 24 has a dedicated measurement circuit. 26. Each sensor circuit 26 energizes and detects the soil conductivity surrounding the ring pair 24 at that level. The measurement circuits 26 are connected to a controller circuit (not shown). Typically, a single controller circuit can control up to five measurement circuits 26, meaning that a single probe 10 will have a pair of controller circuits in order to control ten spaced sensor ring pairs 24. The requirement for dedicated measurement circuits 26 adds substantial cost to the probe 10. Furthermore, each sensor subassembly 22A has its own unique performance parameters, which means that each subassembly 22A must be calibrated individually (and each calibration curve is non-linear). FIG. 2 depicts another prior soil moisture probe.

FIG. 2 is a pair of perspective views of a conventional soil moisture sensor assembly 40 constructed from a flexible circuit board. Instead of sensor rings made from solid metal, these ring pairs 44 are circuits printed onto a flexible substrate 42 that is then rolled into a cylinder so that the sensor rings 44 are ring-shaped. As with the previously-described design, each sensor ring pair 44 has a dedicated measurement circuit 46 associated with it. These measurement circuits 46 are interconnected with the controller circuit 50 by sensor signal conduit 48, which are also both printed on the flexible substrate 42. The controller circuit 50 is connected to the external central control unit (not shown) by control conduit 52.

This flex-circuit sensor assembly 40 suffers from essentially the same problem as the prior device of FIG. 1. While assembly of the probe is simplified because of the use of the flexible substrate 42, it also suffers from the same cost and calibration problems as the prior brass ring version. Furthermore, since this sensor assembly 40 is a single piece, it is virtually impossible to repair any part of the assembly 40 in the event of partial failure. This tends to add additional cost to the operation of this type of probe.

FIG. 3 is provided to illustrate the way in which the soil moisture probe data is generally utilized. This figure is a sample table depicting the curves produced by a conventional soil moisture probe of FIG. 1 (or the sensor assembly [40] of FIG. 2). Each sensor subassembly [22A or 22B] uses a capacitive sensor element to measure the reactance of the soil [8] surrounding it (and the probe [10]). In some versions, the susceptance of the surrounding soil [8] is measured. In either case, the measured value can be correlated to the moisture content of the soil.

Since the probe [10] is buried in a vertical orientation, the subassemblies [22A or 22B] will measure the soil moisture at its own unique (and pre-determined) depth. The example depicted here is what the top three subassemblies [22A] of FIG. 1 may experience over a prolonged period of time. The calculated moisture determined within the soil will be affected by temperature (also a function of the depth of the sensor), level of moisture in the surrounding soil, as well as any conductive substances (such as sodium-based fertilizers) that are present in the soil. As the depth increases, it would be expected that the reactance (for example) would reduce, thereby indicating that the moisture level is dropping. The farmer's mission is to apply just enough irrigation water so that the deepest roots of the plants receive sufficient water and fertilizer, without overwatering (which wastes water and fertilizer). It is believed that the device of the present invention, and its operation, provides a low-cost soil moisture sensing probe that is more accurate and more easily calibrated than any of the prior probe designs.

SUMMARY OF THE INVENTION

In light of the aforementioned problems associated with the prior devices and systems, it is an object of the present invention to provide a Soil Moisture and Electrical Conductivity Probe. The soil moisture probe should employ brass ring pairs, wherein each pair incorporates dual feedpoints. There should be a single main control circuit for operating the plurality of sensor ring pairs in a multiplexed approach. In order to allow for multiplexed operation, each sensor ring pair should include a signal tuning assembly. The signal tuning assembly should include apparatus for attenuating the signal noise at each sensor ring pair, as well as apparatus for matching the ring-pair to ring-pair lead impedance. It is a further goal that the temperature of each ring pair be individually detected to improve the accuracy of all of the sensor ring pairs. This temperature sensing should be done by multiplexing a single reference voltage with all of the sensor rings, and by implementing a thermistor at each sensor ring pair.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a Soil Moisture and Electrical Conductivity Probe.

Figure 1:
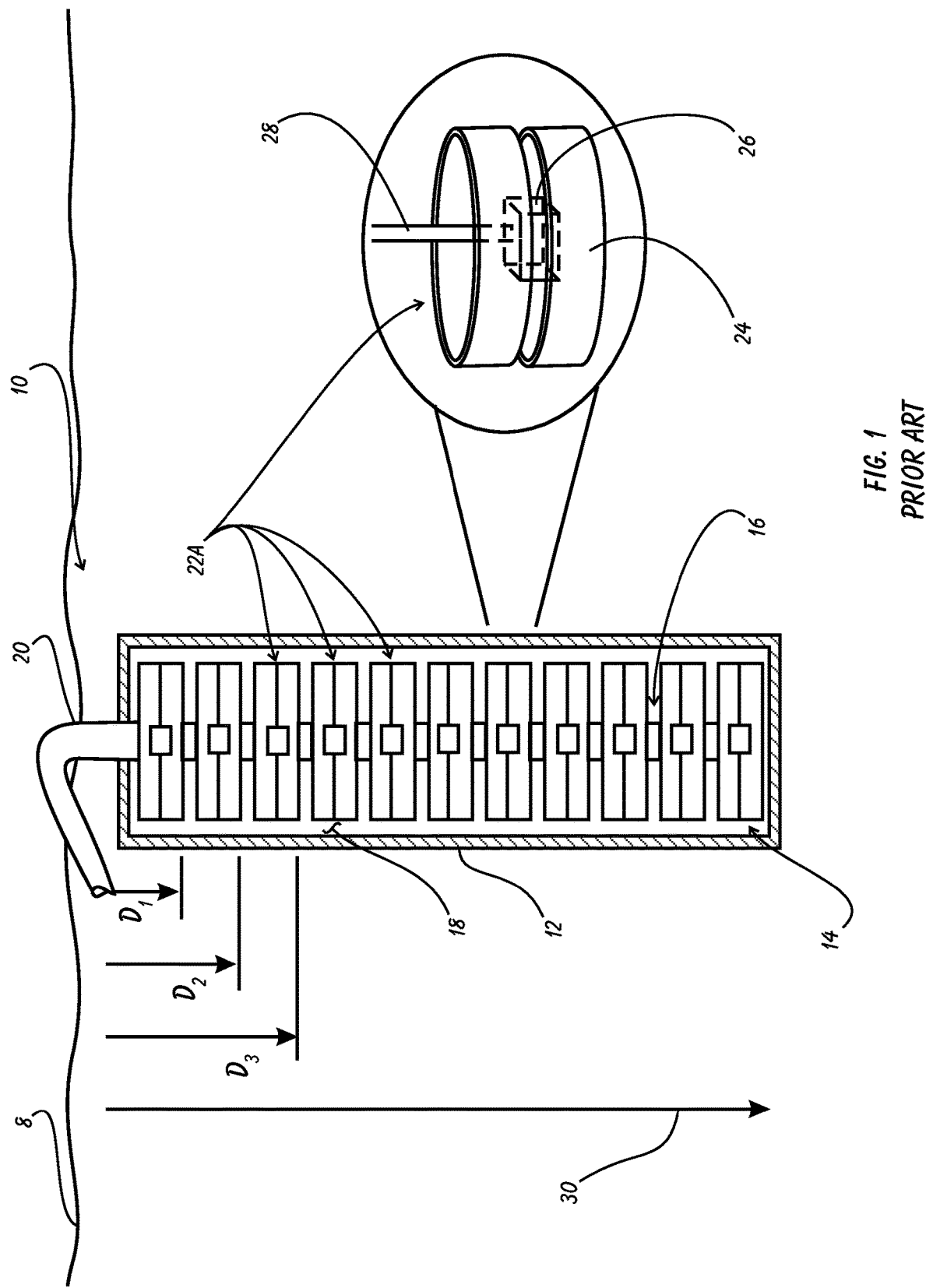
FIG. 1 is a cutaway side view of a conventional soil moisture probe.
Figure 2:
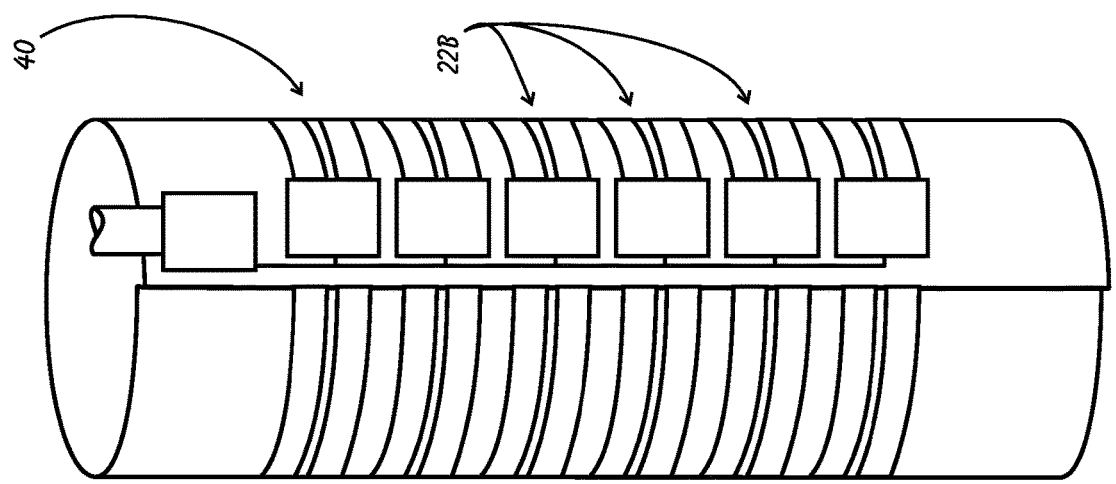
FIG. 2 is a pair of perspective views of a conventional soil moisture sensor assembly constructed from a flexible circuit board.
Figure 2:
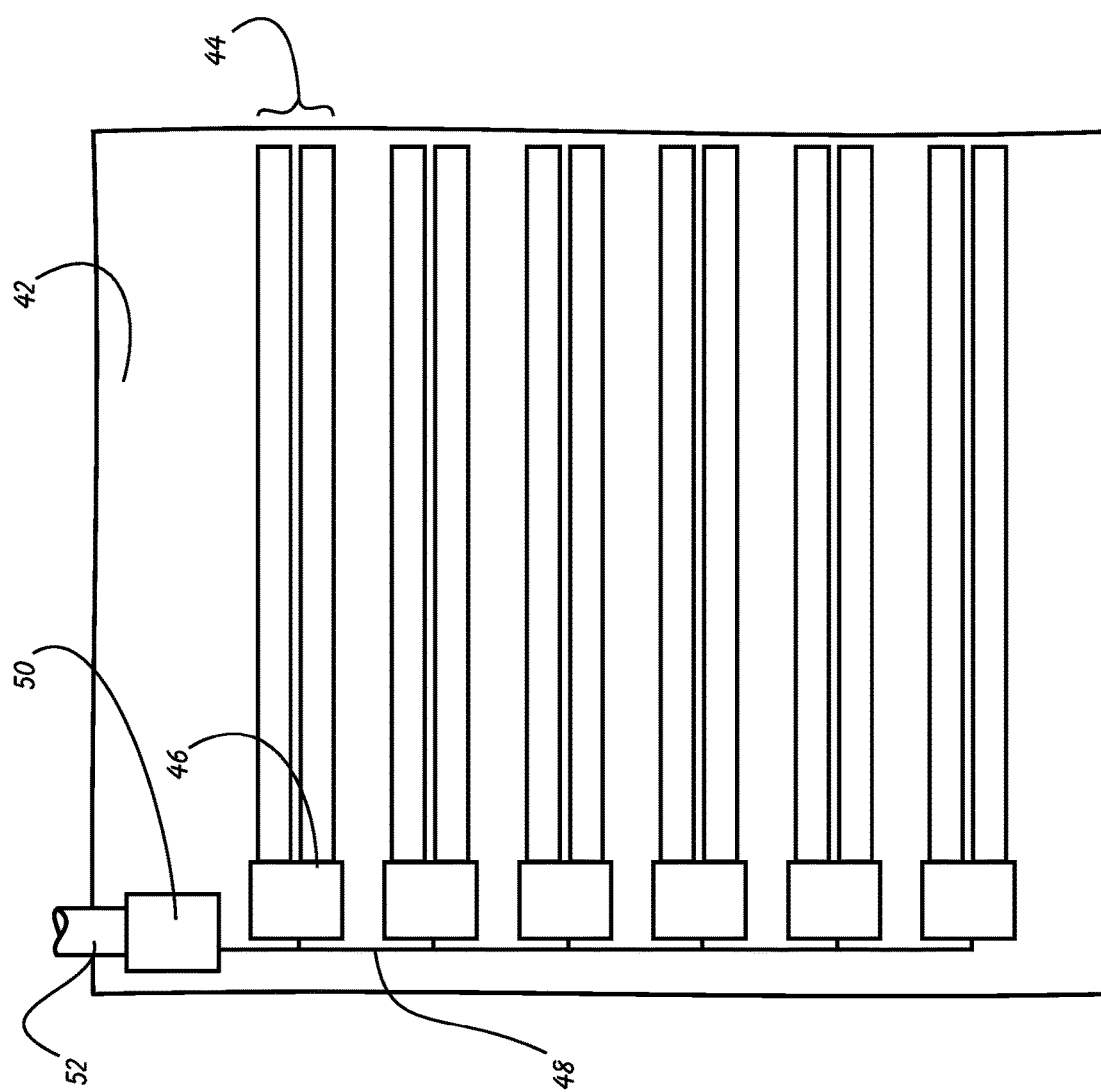
Figure 3:
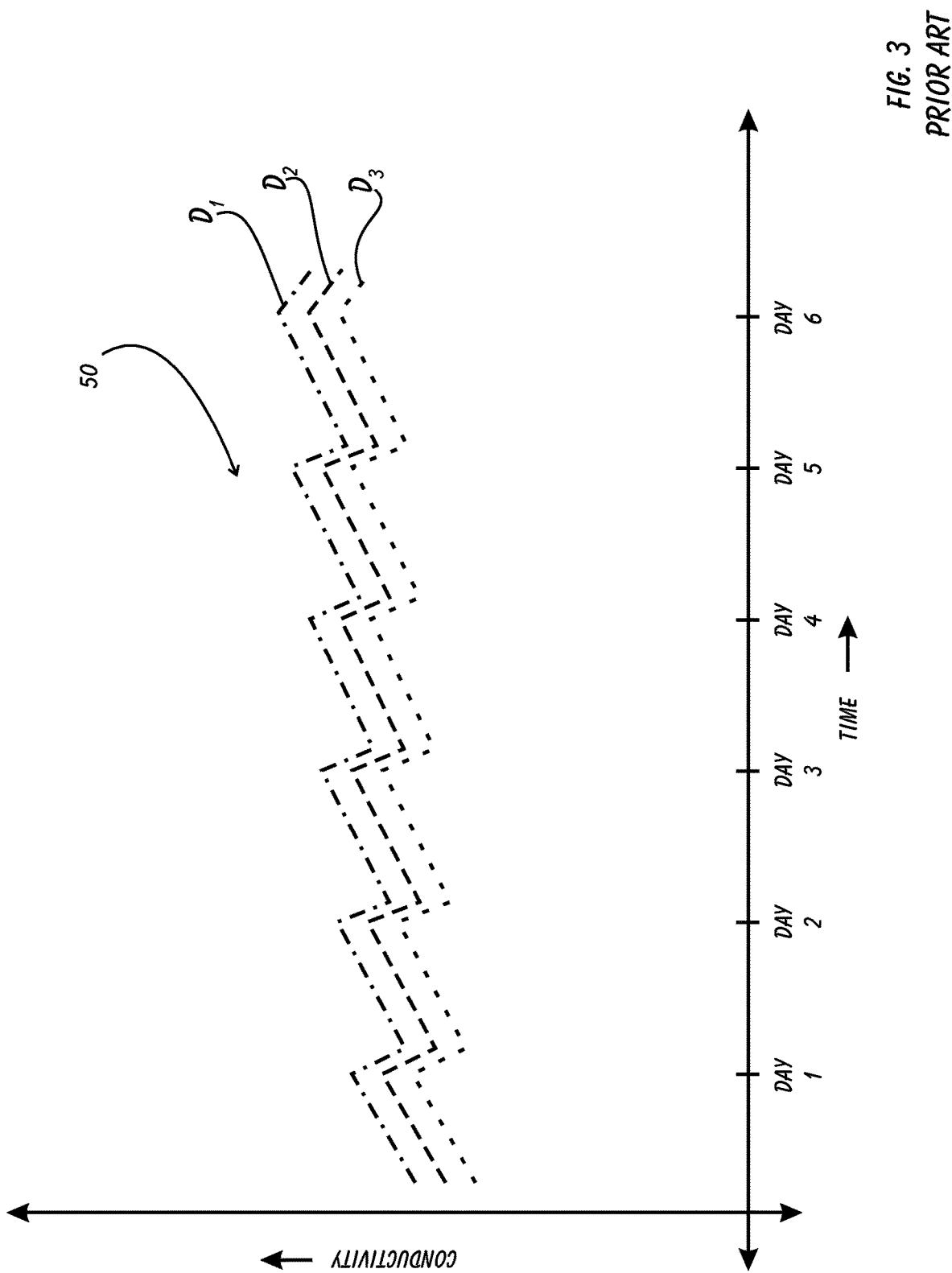
FIG. 3 is a sample table depicting conductivity curves produced by a conventional soil moisture probe of FIG. 1.
Figure 4:
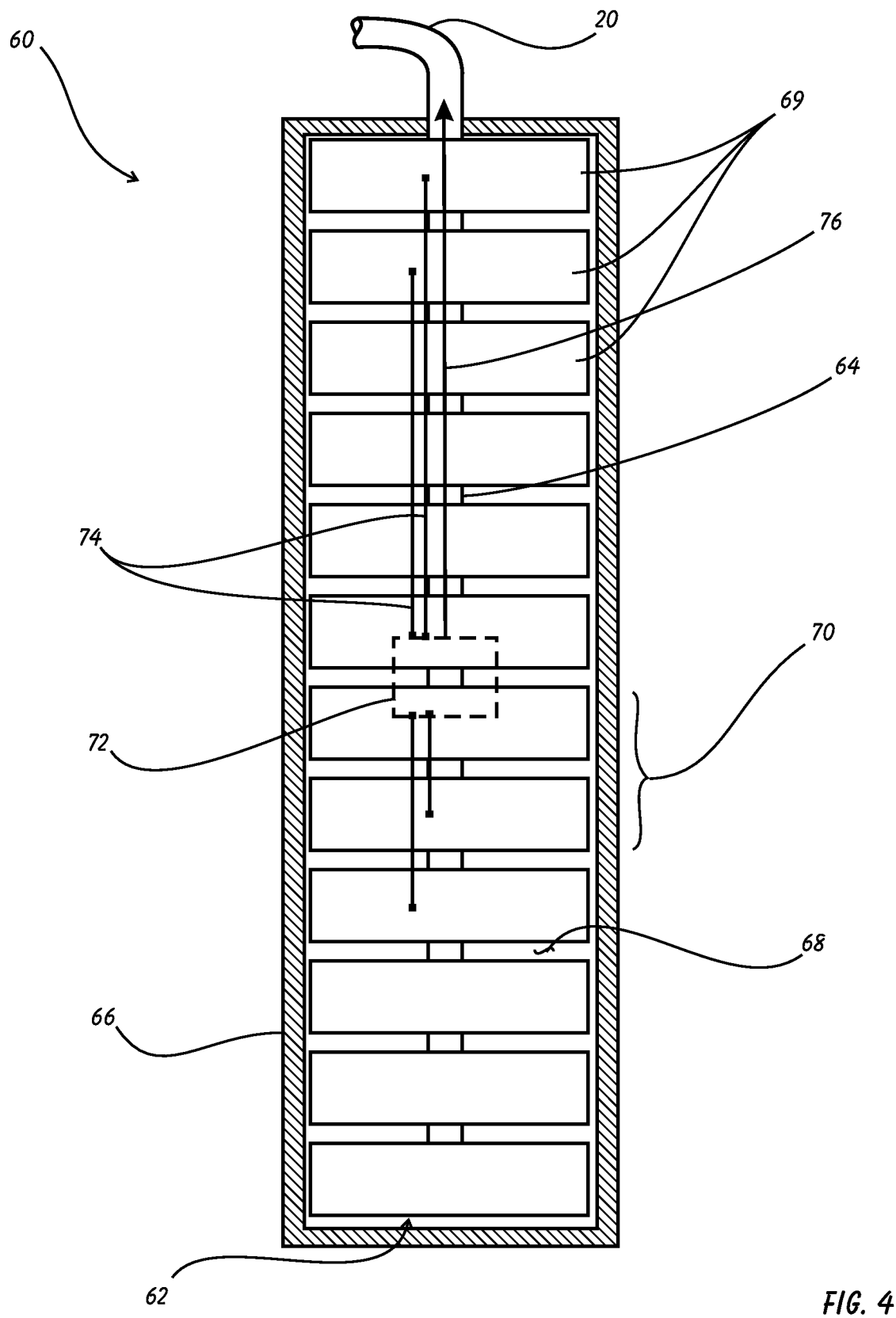
FIG. 4 is a cutaway side view of a preferred embodiment of the improved soil moisture probe of the present invention.

The present invention can best be understood by initial consideration of FIG. 4. FIG. 4 is a cutaway side view of a preferred embodiment of the improved soil moisture probe 60 of the present invention. The probe 60 is designed to improve upon the prior probes by: (1) reducing manufacturing cost of the probe; (2) increasing reliability and durability of the probe; and (3) dramatically improving accuracy and stability of the probe output. These objectives are met by making a fundamental change in the construction and operation of the probe 60, as will be discussed further below.

The probe 60 is housed within a non-metallic housing 66, such as PVC or other suitable material. In this case, however, the wall thickness of the housing 66 is much thinner than prior probes for the reasons set forth below after a discussion of the internal components of the probe 60.

The sensor assembly 62 of this probe 60 is also very distinct as compared to the prior assemblies [14 and 40]. There are a plurality of sensor rings 70 attached to a central base frame 64, and distributed over the length of the interior of the housing 66 in spaced relation. These rings 70 are preferably made from thin brass material, just as were the rings [24]. These rings 70 are somewhat different in their configuration, as compared to the solid rings of the prior art. Each ring 70 is actually made from two semi-circular arcs of brass sheet material. The purpose for this is to reduce the distance over which the sensed capacitance must travel through the sensor ring 70. These provide for two "feedpoints" at each sensor ring 70. The reduced signal travel translates into reduced impedance and potential signal noise. More detail regarding the ring 69 design is provided below in connection with FIGS. 6 and 7.

The key structural distinction over the prior art sensor assemblies [22A and 22B] is that in this sensor assembly 62, there is only a single "main" control circuit 72 driving all of the sensor rings 70 in the probe 60. Each ring 70 is interconnected with the main control circuit 72 by a sensor conduit 74. The main control circuit 72 connects to the control conduit 20 (and the remote main control system) by control cable 76 (in this embodiment).

Using only a single main control circuit 72 to serve several individual sensor rings 70 mandates multiplexing the sensors 70. Only one sensor 70 is activated at a time, with each sensor 70 being activated sequentially in repeated fashion. Since there is no need to have simultaneous readings from the different sensors 70, this approach works perfectly well. Furthermore, the elimination of all but one control circuit substantially reduces cost.

As discussed above, the wall thickness of the housing 66 is approximately 25% thinner than the housing [12] of the prior probes. This is possible because the interstitial chamber 68 of this probe 60 is filled with expandable foam (similar to insulating foam sealant) during assembly. The introduction of foam to the interstitial chamber 68 of the probe 60 is generally contrary to conventional wisdom because it permanently encases the contents of the chamber 68, and prevents any disassembly (such as for repair). The reason why it has been found to be particularly desirable for the soil moisture probe 60 to be foam-filled is because is adds rigidity to the probe 60, which is the reason why the wall thickness of the housing 66 can be thinner than previously available. A thinner housing wall has been demonstrated to improve sensitivity of the sensor rings 70, thereby improving overall system performance. A further benefit is that the foam material within the chamber 68 will prevent convection heat transfer throughout the chamber 68. As can be imagined, the top of the probe 60 is by definition closer to the surface of the soil 8. Consequently, it can tend to experience a much wider range of temperatures due to its proximity to the outside environment. In the prior probes, these temperature swings at the top of the housing [12] would be quickly transferred throughout the chamber [18], thereby introducing measurement error at each of the sensor subassemblies [22A or 22B]. Filling the housing 66 with foam largely eliminates any heat transfer along the length of the probe 60, and therefore reduces the measurement error that would normally be present. Another benefit of the foam filling is that the foam serves to encase the electronics and wiring within the interior of the probe 60. If there is an unfortunate perforation to the housing 66, which would normally allow moisture to intrude upon and damage the internal components, it is less likely to cause damage because the foam acts as a moisture barrier. There are three additional features important to the substantial benefits provided by the instant design that are discussed below in connection with FIG. 5.

Figure 5:
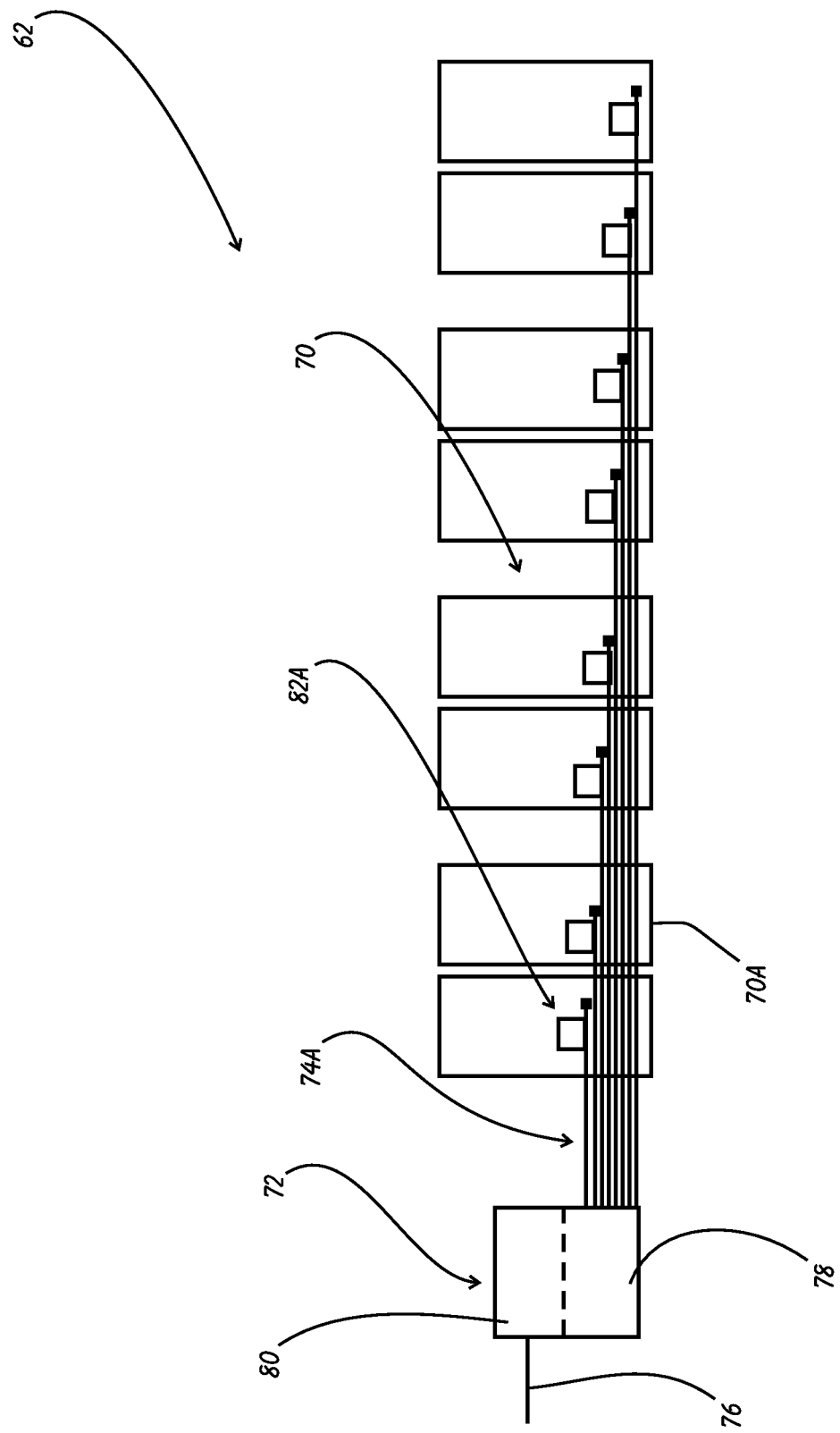
FIG. 5 is a partial block diagram of the wiring of the sensor assembly of the probe of FIG. 4.

FIG. 5 is a partial block diagram of the wiring of the sensor assembly 62 of the probe [60] of FIG. 4. Since the rings 70 are being operated by a single common main control circuit 72, it is critical that the electrical parameters for each ring 70 are consistent so that calibration and operation of the different rings 70 is consistent (so that noise is reduced and sensor-to-sensor cable impedance is consistent and optimized). To that end, a signal tuning assembly 82A is installed in-line on each sensor conduit 74A between the main control circuit 72 and the sensor ring (e.g. 70A—the first ring on the left in this depiction). The signal tuning assembly 82A comprises a coiled portion of the leads making up the sensor conduit 74A and a sleeve encapsulating the coil that is made from ferrite metal, or other suitable material to prevent RF currents generated from EMF fields, either from other coils or other cables, from being created in this set of leads. This assembly 82A can also be described as an "inductor," which utilizes the magnetic field of the sleeve and its effect on the coiled portion of the leads to minimize the effect of these external EMF fields on the signal from the ring 70.

The coiled portion of leads is configured differently for each individual ring 70. The point is that each ring 70 has effectively the identical length of sensor conduit lead. This equalizes the signal delay time to each ring 70, as well as any impedance effects. As should be obvious, the further that the particular ring 70 is away from the main control circuit 72, the fewer wraps making up the coil in the tuning assembly (e.g. 82A). The ferrite sleeve serves to block incident electronic signals from inadvertently creating signal noise with the coil.

An operational choice to further improve accuracy is related to the frequency at which the sensors 70 are operated. Traditionally, sensor rings are operated a variable frequencies at somewhere between fifty (50) and one hundred and fifty (150) MHz. In the instant design, the control circuit 72 operates all sensors 70 at approximately two hundred (200) MHz. In addition to the need for stability and consistency between sensors 70, the other reason to choose such a substantially high fixed frequency is that the relation of permittivity (hence capacitance reactance/susceptance) to frequency becomes very flat and linear around the 200 MHz point. As a result, the calibration of the sensors 70 at this frequency is very predictable and therefore reliable.

Figure 6:
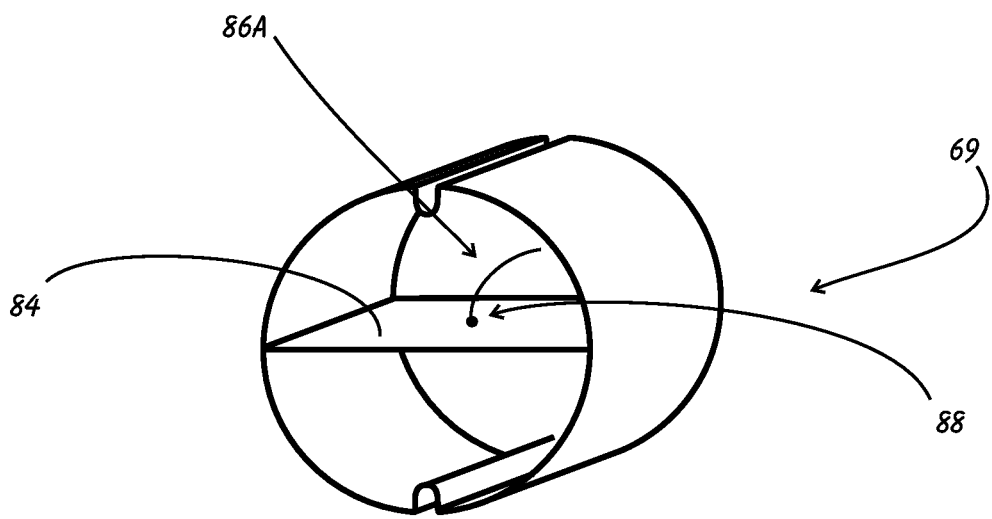
FIG. 6 is a perspective view of a sensor ring of the sensor assembly of the probe of FIG. 4.
Figure 7:
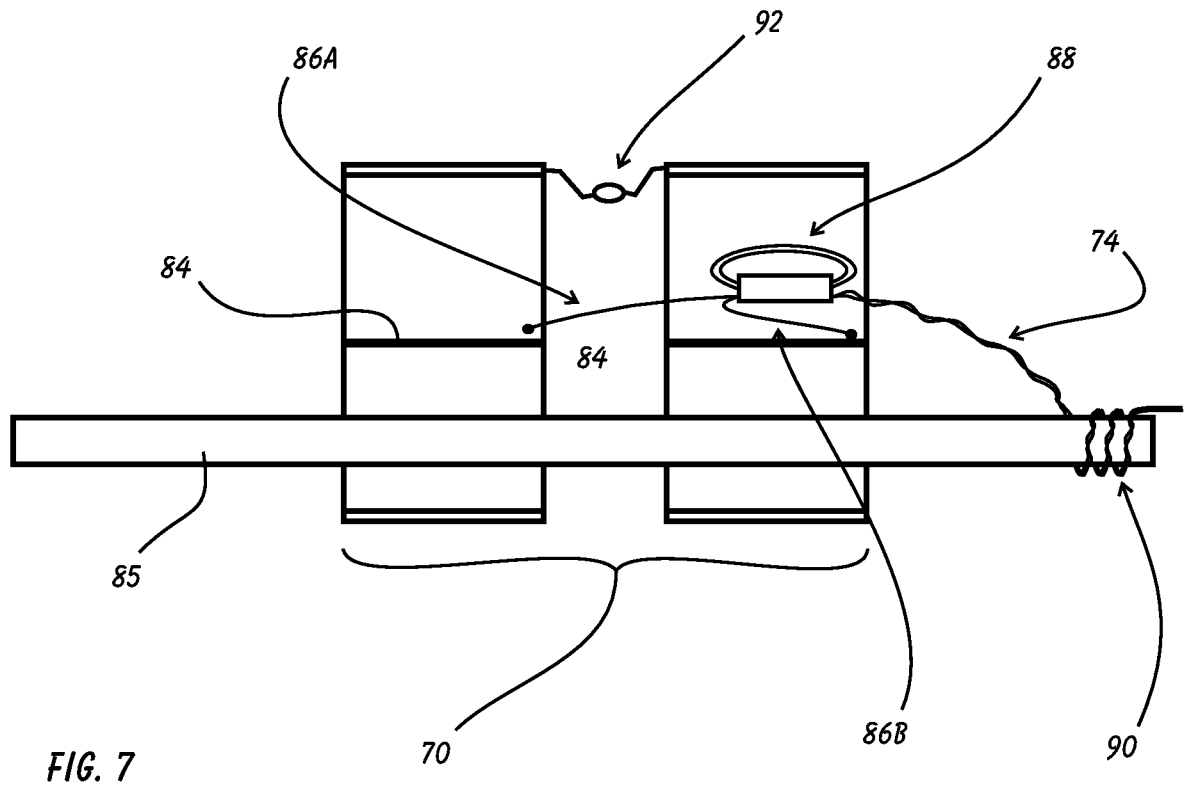
FIG. 7 is a partial cutaway side view of a ring pair of the sensor assembly of the probe of FIG. 4.

To further optimize cost and complexity, the main control circuit 72 is actually a dual-role device. It is made up of the multi-sensor measurement subcircuit 78 (which drives the sensors 70 in multiplexed fashion), and the transceiver subcircuit 80, which communicates with the external central control unit (not shown) by the control cable 76. FIGS. 6 and 7 provide additional detail regarding the sensor rings 69.

FIG. 6 is a perspective view of a sensor ring 70 of the sensor assembly of the probe of FIG. 4. Each sensor ring 69 has a cross-connect member 84 bisecting the circular perimeter ring. The cross-connect member 84 provides an attachment point 88 for the leads 86A centered within the ring 69. This central lead attachment point 88 results in the "dual feedpoint" discussed above. Additionally, the cross-connect member 84 shorts out the two opposing sides of the ring 69, further preventing unwanted noise from EMF. Additional detail regarding the signal tuning assembly [e.g. 82A] discussed in FIG. 5 is provided in FIG. 7.

FIG. 7 is a partial cutaway side view of a ring pair 70 of the sensor assembly of the probe of FIG. 4. As shown, the leads 86A, 86B attach to the cross-connect members 84 of each ring in the pair 70. These and the rest of the ring pairs 70 of the sensor assembly [62] are attached to, and supported by (at least for assembly) a non-metallic backbone member 85. Each pair of leads 86A, 86B forms a sensor conduit 74 for the ring pair 70.

After leaving the rings 69, the leads 86A, 86B are coiled around the noise-attenuating sleeve 88 (the ferrite sleeve discussed previously). The pair of leads 86A, 86B then extends towards the main control circuit [72]. The leads 86A, 86B are wrapped around the exposed section of backbone member 85 adjacent to the pair 70 in wire coil 90. As discussed previously, the sleeve 88 and coil 90 combine to form the signal tuning assembly [e.g. 82A], with the properties discussed therein.

Figure 8:
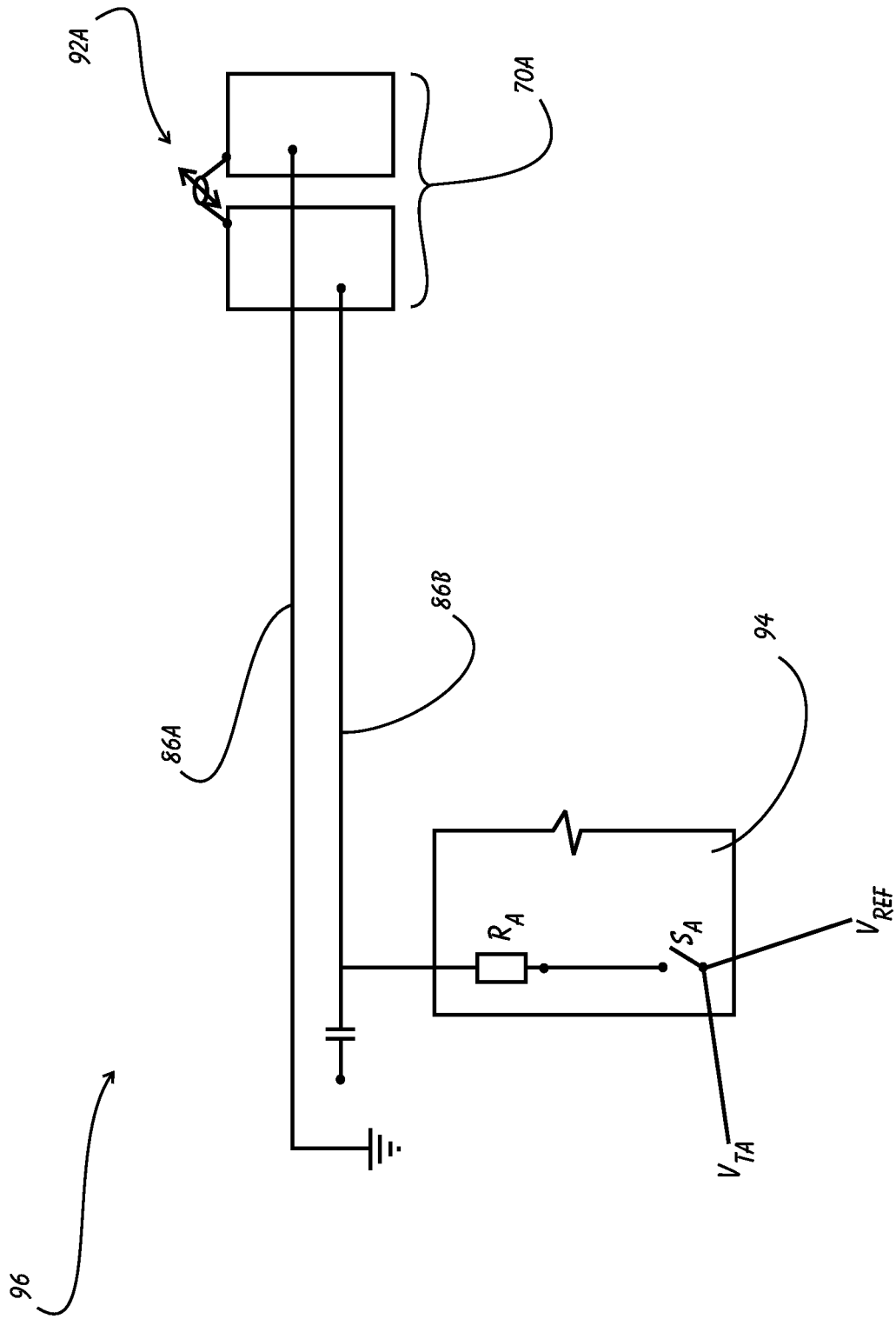
FIG. 8 is a schematic view of a preferred embodiment of the integrated temperature sensing system of the moisture probe of the present invention.

A final novel feature of the system of the present invention relates to the ability to continuously calibrate each individual sensor ring pair 70 for temperature swings. As can be imagined, those ring pairs 70 closer to the surface of the soil will tend to experience greater temperature swings than will the pairs 70 that are deeper in the ground. While it is well-known that temperature has a great effect on the calibration curves of the pairs 70, the prior art sensor assemblies included only a single temperature sensor to calibrate the entire sensor assembly. In the instant design, a thermistor device 92 is included at each ring pair 70. FIG. 8 describes the operation of this novel system.

FIG. 8 is a schematic view of a preferred embodiment of the integrated temperature sensing system 96 of the moisture probe of the present invention. As discussed above, each ring pair (e.g. 70A) has a dedicated thermistor 92A interconnecting the rings 69.

The impedance in the loop (ring pair 70A and leads 86A and 86B) will change when thermistor 92A resistance changes in response to temperature changes. The reference circuit 94 is used to determine the change in resistance, and therefore derive the temperature of the ring pair (e.g. 70A).

A further unique aspect of the design is that the individual thermistors [92] are multiplexed to a single reference/sensing circuit 94, in order to reduce cost without reducing functionality.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A device for determining the moisture content in the surrounding material, comprising:
    an elongate housing defining an internal chamber, said elongate housing submerged in the surrounding material;
    a multiplexed sensor assembly contained within said internal chamber, said multiplexed sensor assembly comprising:
        a plurality of sensor ring pairs in relative spaced relation, each said sensor ring pair comprising a generally circular ring portion and a cross-connect member, bisecting said generally circular ring portion, whereby said cross-connect member is in electrical connection with said generally circular ring portion at its attachment points; and
        a main control circuit device electrically connected to all of said sensor ring pairs;
    a control conduit extending from said main control circuit whereby said control conduit is interconnectable to a central controller circuit external to said housing; and
    interstitial foam between said ring pairs and said housing.

2. The device of claim 1, wherein each said ring pair further comprises a signal tuning assembly in said electrical connection between said ring pair and said main control circuit.

3. The device of claim 2, wherein each said ring pair further comprises a temperature sensor.

4. The device of claim 3, wherein said main control circuit comprises transceiver subcircuit and multi-sensor measurement subcircuit, said multisensor measurement subcircuit electrical connection with all of said ring pairs and said transceiver subcircuit interconnecting said multi-sensor measurement subcircuit and said control conduit.

5. The device of claim 4, wherein said signal tuning assembly includes signal noise attenuating apparatus and a lead impedance matching apparatus.

6. The device of claim 5, further comprising single reference temperature signal interconnectable to all said ring pairs individually.

7. The device of claim 1, wherein each said ring pair further comprises a temperature sensor.

8. The device of claim 7, further comprising a single reference temperature signal interconnectable to all said ring pairs individually.

9. The device of claim 1 wherein each said ring pair further comprises a signal tuning assembly in said electrical connection between said ring pair and said main control circuit and
    said signal tuning assembly includes signal noise attenuating apparatus and a lead impedance matching apparatus.

10. The device of claim 1, wherein said main control circuit comprises transceiver subcircuit and multi-sensor measurement subcircuit, said multisensor measurement subcircuit electrical connection with all of said ring pairs and said transceiver subcircuit interconnecting said multi-sensor measurement subcircuit and said control conduit.

11. A soil moisture sensor device for determining subterranean soil moisture levels, comprising:
    an elongate housing defining an internal chamber and an outer wall of non-conductive material having a wall thickness of less than 2 millimeters, said elongate housing submerged in the soil;
    a multiplexed sensor assembly contained within said internal chamber, said multiplexed sensor assembly comprising:
        a plurality of sensor ring pairs in relative spaced relation, each said sensor ring pair comprising an outer ring portion and a cross-connect portion bisecting said outer ring portion and in electrical connection therewith; and
        a single main control circuit device electrically connected to all of said sensor ring pairs;
    a control conduit extending from said main control circuit whereby said control conduit is interconnectable to a central controller circuit external to said housing; and
    interstitial foam between said ring pairs and said housing.

12. The device of claim 11, wherein each said ring pair further comprises a temperature sensor.

13. The device of claim 12, further comprising single reference temperature signal interconnectable to all said ring pairs individually.

14. The device of claim 11 wherein each said ring pair further comprises a signal tuning assembly in said electrical connection between said ring pair and said main control circuit.

15. The device of claim 14, wherein said signal tuning assembly includes signal noise attenuating apparatus and a lead impedance matching apparatus.

16. The device of claim 11, wherein said main control circuit comprises transceiver subcircuit and multi-sensor measurement subcircuit, said multisensor measurement subcircuit electrical connection with all of said ring pairs and said transceiver subcircuit interconnecting said multi-sensor measurement subcircuit and said control conduit.

17. The device of claim 11, further comprising interstitial foam between said ring pairs and said housing.

\* \* \* \* \*